United States Patent
Fujieda

[19]

[11] Patent Number: 6,079,828
[45] Date of Patent: Jun. 27, 2000

[54] OPHTHALMIC MEASUREMENT APPARATUS

[75] Inventor: Masanao Fujieda, Toyohashi, Japan

[73] Assignee: Nidek Co., Ltd., Aichi, Japan

[21] Appl. No.: 09/032,980

[22] Filed: Mar. 2, 1998

[30] Foreign Application Priority Data

Mar. 4, 1997 [JP] Japan ................................. 9-067463

[51] Int. Cl.[7] .................................................. A61B 3/14
[52] U.S. Cl. .......................................... 351/206; 351/211
[58] Field of Search .................................. 351/205, 206, 351/211, 212, 221; 600/405

[56] References Cited

U.S. PATENT DOCUMENTS

| | | |
|---|---|---|
| 4,917,458 | 4/1990 | Matsumura . |
| 5,000,181 | 3/1991 | Katsuragi ................................ 351/206 |
| 5,432,596 | 7/1995 | Hayashi . |
| 5,463,430 | 10/1995 | Isogai et al. . |
| 5,500,697 | 3/1996 | Fujieda . |
| 5,585,872 | 12/1996 | Kohayakawa . |

FOREIGN PATENT DOCUMENTS 6-51023  7/1994  Japan .

8-266474  10/1996  Japan .

*Primary Examiner*—George Manuel
*Attorney, Agent, or Firm*—Oliff & Berridge, PLC

[57] ABSTRACT

An ophthalmic measurement apparatus for observing or measuring an eye to be examined by positioning the apparatus so as to have a predetermined positional relationship with the eye, the ophthalmic measurement apparatus comprising an alignment target projecting device for projecting an alignment target onto a cornea of the eye, an alignment device provided with a photographing optical system for photographing an image of the projected alignment target by photoelectric imaging elements to perform an alignment based on condition of the alignment target image photographed by the photoelectric imaging elements, a measurement target projecting device for projecting a target for measurement onto the cornea of the eye, a measurement device for measuring a corneal shape of the eye based on an image of the projected target for measurement photographed by the photoelectric imaging elements, a focal depth varying device for making a focal depth of the image photographed by the photoelectric imaging elements variable and a changeover device for switching the focal depth, which is made to be variable by the focal depth varying device, upon the alignment and upon the measurement.

11 Claims, 6 Drawing Sheets

OPHTHALMIC MEASUREMENT APPARATUS

BACKGROUND OF THE INVENTION

1. Field of the Invention

The present invention relates to an ophthalmic measurement apparatus, and more particularly to an ophthalmic measurement apparatus for observing or measuring an eye to be examined by positioning the apparatus so as to have a predetermined positional relationship with the eye.

2. Description of Related Art

Regarding an ophthalmic measurement apparatus which requires positional adjustment so as to have a predetermined positional relationship between an eye to be examined and an apparatus, it is conventionally known to utilize a corneal reflection point. In such a method, the apparatus projects an alignment target onto a cornea of the eye, and photographs a corneal reflection point with photographing elements included in an alignment optical system so as to display the image of the corneal reflection point on a monitor. Alignment is to be performed with observing the image. To have a predetermined positional relationship between the image of a corneal reflection point and a reticle mark (an alignment mark), which is generated either optically or electrically, positional adjustment is made in horizontal directions and vertical directions. In order to make the image of a corneal reflection point the smallest, adjustment in forward and backward directions is made by judging from a blur of the image.

Referring to a measurement means for measuring an eye to be examined, it is known, for example, an apparatus to detect a placido ring target which is projected onto relatively broad part of a cornea of the eye with photographing elements included in a photographing optical system, and measures distribution of corneal curvature in detail based on the detected signal. In this case, a focal depth is made to be comparatively deep in a manner of providing a diaphragm which is adjusted to be appropriate in size in an optical path of a photographing optical system, so that a sharp photographed image over an anterior part of the eye from its center to its periphery can be obtained without being influenced by a position of a projected target image on a cornea of the eye.

However, in a photographing optical system which is required to photograph an image sharply as described above, when an alignment utilizing blur of an image of a corneal reflection point is to be performed, different sets of photographing elements are required for a photographing optical system and for an alignment optical system due to the difference in a focal depth which each optical system requires.

SUMMARY OF THE INVENTION

The present invention has been made in view of the above circumstances and has an object to overcome the above problem and to provide an ophthalmic measurement apparatus for observing or measuring an eye to be examined, sharing the same optical elements used for a photographing optical system and an alignment optical system, and yet capable of ensuring easiness in alignment as well as sharpness in photographed images.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic measurement apparatus of this invention comprises alignment target projecting means for projecting an alignment target onto a cornea of the eye, alignment means provided with a photographing optical system for photographing an image of the projected alignment target by photoelectric imaging elements to perform an alignment based on condition of the alignment target image photographed by the photoelectric imaging elements, measurement target projecting means for projecting a target for measurement onto the cornea of the eye, measurement means for measuring a corneal shape of the eye based on an image of the projected target for measurement photographed by the photoelectric imaging elements, focal depth varying means for making a focal depth of the image photographed by the photoelectric imaging elements variable and changeover means for switching the focal depth, which is made to be variable by the focal depth varying means, upon the alignment and upon the measurement.

In another aspect of the present invention, the ophthalmic measurement apparatus comprises alignment target projecting means for projecting an alignment target onto a cornea of the eye, alignment means provided with a photographing optical system for photographing an image of the projected alignment target by photoelectric imaging elements to perform an alignment based on condition of the alignment target image photographed by the photoelectric imaging elements, first measurement means for measuring a first function of the eye by projecting a first target for measurement onto the eye, and also by detecting the first target image, second measurement means for measuring a second function of the eye by projecting a second target for measurement onto the eye, and also by detecting the second target image utilizing the photoelectric imaging elements and focal depth varying means for making a focal depth of the image photographed by the photoelectric imaging elements variable.

Further, in another aspect of the present invention, the ophthalmic measurement apparatus comprises alignment target projecting means for projecting an alignment target onto a cornea of the eye, alignment means provided with a photographing optical system for photographing an image of the projected alignment target by photoelectric imaging elements to perform an alignment based on condition of the alignment target image photographed by the photoelectric imaging elements, recording means for recording an image of an anterior part of the eye photographed by the photoelectric imaging elements, focal depth varying means for making a focal depth of the image photographed by the photoelectric imaging elements variable and changeover means for switching the focal depth, which is made to be variable by the focal depth varying means, upon the alignment and upon the measurement.

As described above, and in accordance with the present invention, the apparatus enables to obtain a desired focal depth respectively upon alignment and photographing, therefore, the easiness in alignment and the sharpness in photographed images are assured.

BRIEF DESCRIPTION OF THE DRAWINGS

The accompanying drawings, which are incorporated in and constitute a part of this specification illustrated embodi- In the drawings.

DETAILED DESCRIPTION OF THE PREFERRED EMBODIMENTS

Figure 1:
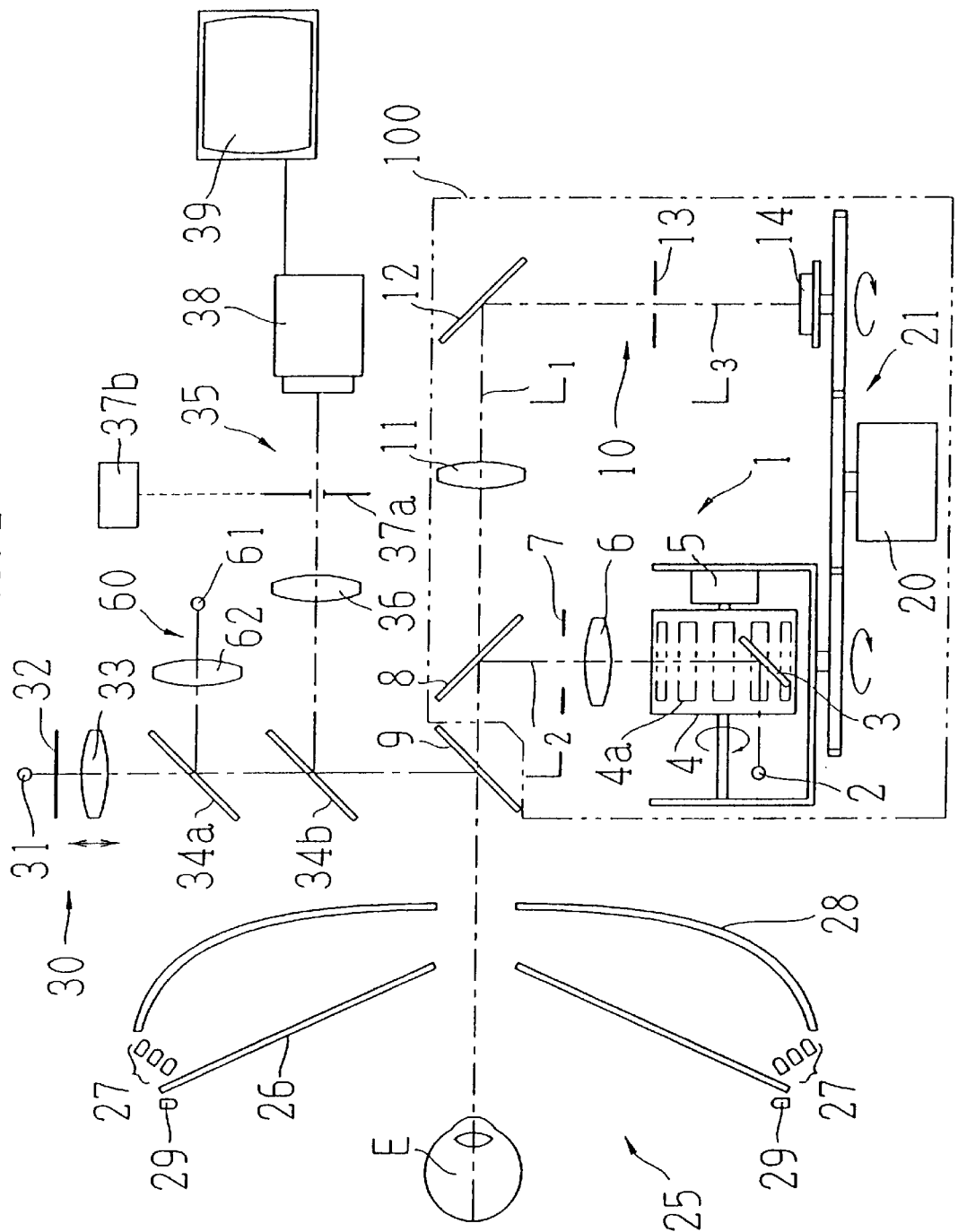
FIG. 1 is a view showing a schematic optical system arrangement of an apparatus according to the first preferred embodiment of the present invention.

A detailed description of an ophthalmic measurement apparatus embodying the present invention will now be given referring to the accompanying drawings. FIG. 1 is a view showing a schematic optical system arrangement of the apparatus according to the first preferred embodiment. The apparatus of the first embodiment has two measurement functions, which are eye refractive power measurement function and a corneal shape measurement function. The optical system can be roughly divided into an eye refractive power measuring optical system, a fixation target optical system, an alignment target projecting optical system, a target projecting optical system for measuring a corneal curvature and a target detection and observation optical system.

(Eye refractive power measurement optical system)

An eye refractive power measuring optical system 100 consists of a slit projecting optical system 1 and a slit-image detecting optical system 10. The slit projecting optical system 1 has a construction as follows. 2 is a slit illumination light source which emits lights within a range of near infrared rays, 3 is a mirror. 4 is a rotation sector with cylinder shape which is made to be rotated in the fixed direction with the fixed velocity by a motor 5. Numbers of apertures 4a are provided on the side face of the rotation sector 4. 6 is a projecting lens, and the light source 2 is at the conjugate position with a vicinity of a cornea of an eye E to be examined with respect to the projecting lens 6. 7 is a limit diaphragm, and 8 is a beam splitter by which the optical axis L1 opposite to the eye E and the optical axis L2 of the slit projecting optical system are made to be coaxial.

The light within a range of near infrared rays which is emitted from the light source 2 is reflected by the mirror 3 and then illuminates the slit apertures 4a of the rotation sector 4. The slit light bundle scanned by rotation of the rotation sector 4 successively passes through the projecting lens 6 and the limit diaphragm 7 to be reflected by the beam splitter 8. Then, the slit light bundle transmits a beam splitter 9 which makes the optical axis L1 and the optical axis of the fixation target optical system and the observation optical system coaxial, and converges in the vicinity of the cornea of the eye E, so as to be projected onto a fundus of the eye E.

Figure 2:
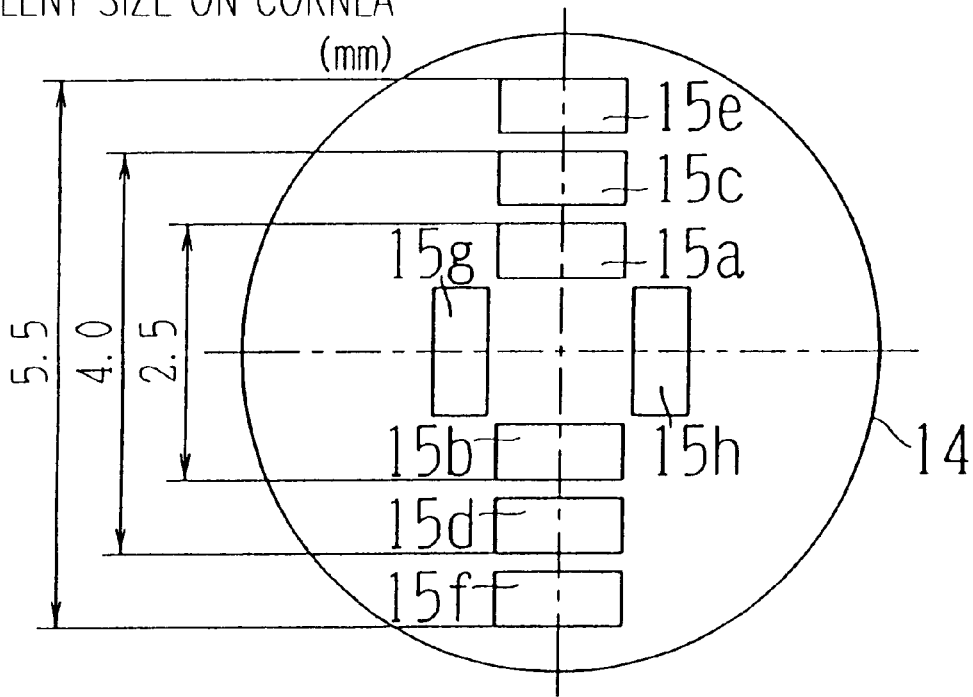
FIG. 2 is a view showing an arrangement of photo-receiving elements (photo-detectors) included in a photo-receiving part shown in FIG. 1.

The slit-image detecting optical system 10 is provided with a photo-receiving lens 11 and a mirror 12, which are arranged on the optical axis L1, as well as a diaphragm 13 and a photo-receiving part 14, which are arranged on the optical axis L3 reflected by the mirror 12. The diaphragm 13 is positioned at the back focal point of the lens 11 through the mirror 12 (that is to say at the conjugate position with respect to a fundus of an eye having emmetropia). As shown in the FIG. 2, the photo-receiving part 14 has eight photo-receiving elements (photo-detectors) 15a–15h, which are at the approximate conjugate positions with respect to the cornea of the eye E on the surface thereof. Six photo-receiving elements (photo-detectors) 15a–15f out of eight photo-receiving elements (photo-detectors) 15a–15h are positioned on the line which passes through the center of the photo-receiving surface (the optical axis L3), so as to make pairs, 15a with 15b, 15c with 15d and 15e with 15f, which are symmetric to each other with respect to the center of the photo-receiving surface (that is to say with the optical axis L3). These three pairs of photo-receiving elements (photo-detectors) of which the configuration distance is set so as to detect refractive power corresponding to respective positions in the meridian direction of the cornea (in FIG. 2, it is denoted by the equivalent size on the cornea). On the other hand, the photo-receiving elements (photo-detectors) 15g and 15h are positioned so as to be symmetric on the line intersecting at the right angle relative to the line passing through the photo-receiving elements (photo-detectors) 15a–15h with the center at the optical axis L3.

In the eye refractive power measurement optical system 100 having above-described construction, a rotation mechanism 21 comprising a motor 20, a gear and the like rotates the components of the slit projecting optical system 1, from the slit illumination light source 2 to the motor 5, on the optical axis L2, and also the photo-receiving part 14 on the optical axis L3 with making the rotations synchronized to each other. In addition, the direction in which the photo-receiving elements (photo-detectors) 15a–15f are placed is set to be correspond to the scanning direction of the slit light bundle projected on the eye E by the slit projecting optical system 1 (the slit light bundle on the fundus is as if to be scanned to the direction intersecting the long side of the slit at the right angle). In the case of the apparatus of the preferred embodiment, the photo-receiving elements (photo-detectors) 15a–15f are placed in the direction corresponding to the direction perpendicularly intersecting the long side of the slit received by the photo-receiving part 14 when the slit light bundle passing through the slit apertures 4a is scanned on a fundus of an eye having hyperopia or myopia exclusive of astigmatism.

(Fixation target optical system)

30 is a fixation target optical system, 31 is a visible light source, 32 is a fixation target and 33 is a projecting lens. The projecting lens 33 fogs the eye E by moving toward the optical axis. 34a and 34b are beam splitters. The light source 31 illuminates the fixation target 32, and the light bundle from the fixation target 32 passes through the projecting lens 33 and the beam splitters 34a and 34b, and then is reflected by the beam splitter 9 and reaches to the eye E, which is being fixed on the fixation target.

(Alignment target projecting optical system)

Numeral 60 denotes an alignment target projecting optical system. 61 is a point light source which emits light within a range of infrared rays, and 62 is a projecting lens. The light emitted from the point light source 61 is projected onto the eye E through the beam splitters 34a, 34b and 9, so that the image of the light source 61 is to be formed on the cornea of the eye E.

(Target projecting optical system for measuring curvature)

A target projecting optical system 25 for measuring a curvature has a structure as follows. 26 is a conic placido-plate provided with an aperture in the center thereof, and there formed ring patterns having numerous light intercepting parts and light passing parts on concentric circles with the center on the optical axis L1. 27 are plural illumination light sources such as LED or the like, the red light (or the near infrared light) emitted from the light sources 27 is reflected by a reflecting plate 28, so as to illuminate the placido-plate from the behind almost evenly. The light bundle having ring patters passed through the light passing parts of the placido-plate 26 is to be projected onto the cornea of the eye E.

(Target detection and observation optical system)

Numeral 35 denotes a target detection and observation optical system. 36 is a photographing lens, and disposed near the back focal point of the photographing lens 36 is a circular diaphragm 37a provided with an aperture of which radius is variable by the operation of a driving device 37b. 38 is a CCD camera. An image of the anterior part of the eye E illuminated by an anterior part illumination light source 29, and also an image of the target projected by the alignment target projecting optical system 60 are reflected by the beam splitter 9 and the beam splitter 34b in succession, thereafter the same passes through the aperture of the diaphragm 37a by the photographing lens 36 so as to be photographed by the CCD camera 38 and be displayed on the TV monitor 39. In addition, the light bundle of the corneal reflection having ring patterns projected by a target projecting optical system 25 for measuring curvature passes through the same optical path as described above, thereafter forms the image of the corneal reflection having ring patterns on the surface of the photographing elements of the CCD camera 38.

Figure 3:
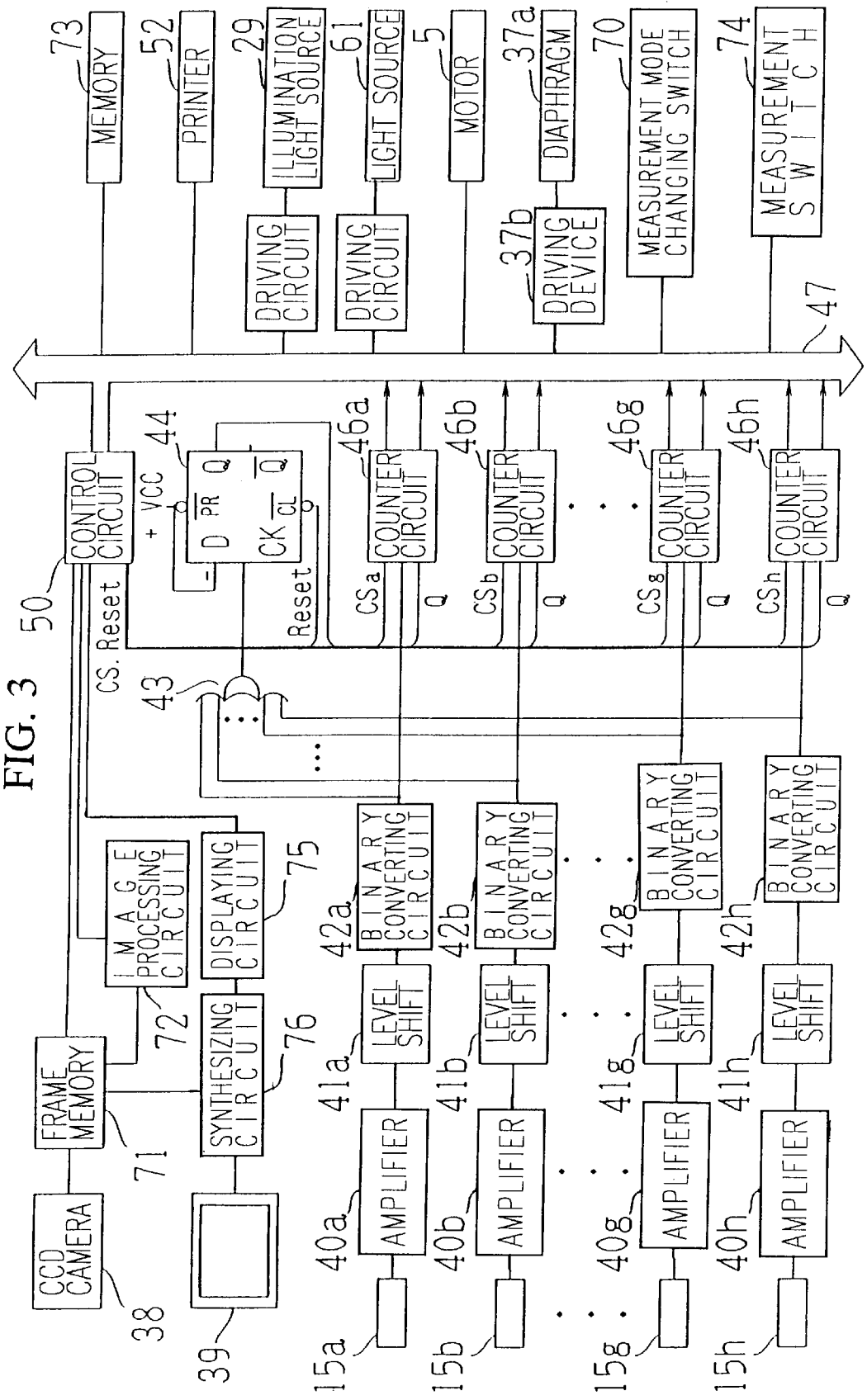
FIG. 3 is a view showing a schematic block diagram of a signal processing system of an apparatus according to the first preferred embodiment of the present invention.
Figure 4:
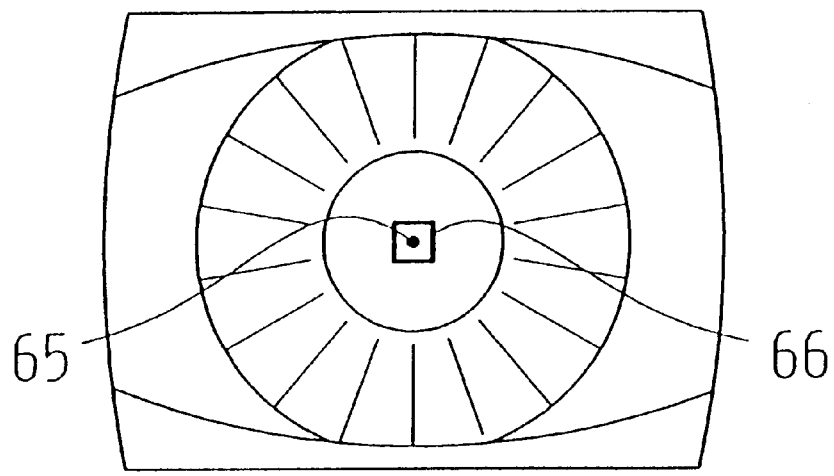
FIG. 4 is a view showing an example of a screen displayed on a monitor upon alignment.

Next, the operations of the apparatus will be described hereinafter with reference to the schematic block diagram of a signal processing system shown in FIG. 3. First, the eye refractive power measurement will be described. An examiner selects a mode for measuring a refractive power by using a measurement mode changing switch 70, and performs alignment while observing the TV monitor 39. An example of a screen displayed on the monitor 39 upon alignment is shown in FIG. 4. The examiner moves the apparatus, so that a target image 65 projected by the point light source 61 for alignment is positioned in the center of the reticle mark (the alignment mark) 66 for aiming (here, a well-known moving means such as a joystick or the like can be utilized), thereafter makes alignment adjustments in the vertical and horizontal directions toward the eye E. Alignment adjustments in the forward and backward directions should be also made in order to bring the target image 65 into focus. Upon the mode for measuring a refractive power measurement mode, the diaphragm 37a is released, accordingly the focal depth of the image photographed by the CCD camera 38 is to be shallow. In the case that an optical system has a shallow focal depth, as the gap from the appropriate working distance becomes wider, the blur of the target image 65 also becomes bigger, therefore the alignment for the working distance can be carried out easily.

When the alignment is completed, the examiner depresses a measurement (starting) switch 74, then the measurement is started responding to the trigger signal generated by the operation. The apparatus executes a preliminary measurement of the refractive power in a conventional way of a refractive power measurement by applying the phase different method. Based on the refractive power obtained by the preliminary measurement, the projecting lens 33 of the fixation target optical system 30 is to be shifted so that the fixation target 32 and the fundus of the eye E are to be at the conjugate positions with respect to the projecting lens 33. Further, the adequate quantity of the diopter is to be fogged. The slit light bundle which is limited by passing through the slit apertures 4a is emitted from the slit projecting optical system 1 and arrives into the eye E through the pupil to be projected onto the fundus. The light bundle of the slit-image, which is reflected by the fundus and has passed the pupil, reaches to the photo-receiving part 14 of the slit-image detecting optical system 10. Here, if the eye E is emmetropia, at the moment the light bundle arrives into the eye E, the photo-voltage is to be generated on the photo-receiving elements (photo-detectors) 15a–15h in the photo-receiving part 14 simultaneously. On the contrary, if there is ametropia in the eye E, the slit-image light reflected by the fundus moves as if it crosses the photo-receiving part 14.

In response to the movement of the slit-image light in the photo-receiving part 14, each of the photo-receiving elements (photo-detectors) 15a–15h generates photo-voltage (there exist the time difference between the time each photo-voltage is generated). The generated photo-voltages respectively go through corresponding amplifiers 40a–40h and the level shift circuits 41a–41h, which are connected to each of the photo-receiving elements (photo-detectors) 15a–15h, thereafter the respective photo voltages are converted to the pulse signals in the binary form with the predetermined threshold level by respective binary converting circuits converted by the binary converting circuits 42a–42h. Continually, respective pulse signals are inputted to counter circuits 46a–46h and an OR circuit 43. In the OR circuit 43, the first rising edge among the pulse signals converted by the binary converting circuits 42a–42h is made to be the rising of the pulse for measurement, and the first rising edge is to be inputted to a flip-flop 44, which comes to next. The flip-flop 44 gives the pulse signals for measurement which includes the time base (rising edge) to the respective counter circuits 46a–46h, and is reset by receiving the Reset signal outputted by the control circuit 50 after all pulse signals are measured.

When the pulse signals converted to the binary form in the binary converting circuits 42a–42h and also the pulse signals for measurement outputted from the flip-flop 44 are inputted to the counter circuits 46a–46h, the counter circuits 46a–46h count and hold the rising time and the time of the pulse-width of the pulse signals in respect with the rising edge (the time base) of the pulse signals for measurement.

The time counted and held by each counter circuit is outputted responding to the call signals (CSa–CSh) generated by the control circuit 50, and then inputted to the control circuit 50 through a data bus 47. The control circuit 50 calculates the time of the corneal center in the meridian direction for measurement (the scanning direction of the slit light bundle) based on the rising time and the time of the pulse-width of respective pulse signals with respect to the time base of respective photo-receiving elements (photo-detectors), which are transmitted from each of the counter circuits 46a–46h. The time of the corneal center can be obtained based on the photo-voltage signals generated by the photo-receiving elements (photo-detectors) 15g and 15h which are positioned on the line intercepting at the right angle with respect to three pairs of the photo-receiving elements (photo-detectors). Consequently, to be obtained is that the time differences (the phase difference) between the corneal center and each of the three pairs of the photo-receiving elements (photo-detectors) which are positioned in the meridian direction for measurement.

Figure 5:
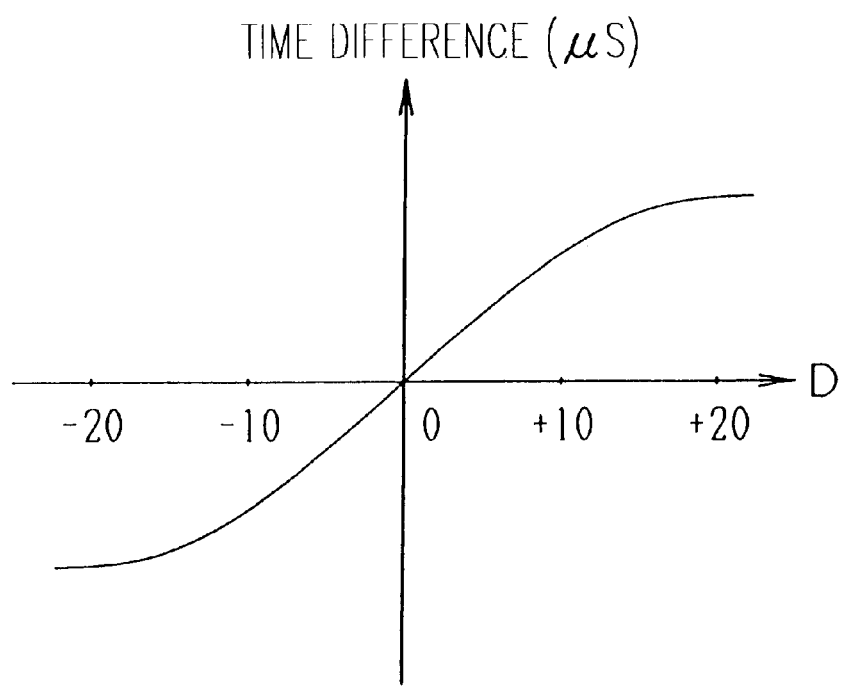
FIG. 5 is a view showing the relationships between the time difference which is detected by the phase-different method and the refractive power.

Once, the time differences at respective corneal parts on one meridian is obtained, these time difference are to be converted into refractive powers. There exist the relationships between the time difference obtained by the phase difference method and the refractive power, which is shown in FIG. 5. Referring to the relationships, the refractive power corresponding to the time difference can be obtained by utilizing the data which are sampled and stored by measuring a model eye of which a refractive power is already known.

Next, by driving the motor 20, the components of the slit projecting optical system 1, from the slit illumination light source 2 to the motor 5, and also the photo-receiving part 14 are made to be rotated 180° around the optical axis with the predetermined intervals (for example, 1°). The refractive power at each rotation position is to be obtained based on the signals from the respective photo-receiving elements (photo-detectors). The refractive power measurement is to be repeated numerous numbers of times, and the results are to be stored after conducting the predetermined processes (calculating the average, the medium value and the like) are carried out. The parameters S, C and A, which are the same as the parameters conventionally used, are calculated through the predetermined processes to the refractive power in respective meridian directions.

The detail of the above-described measurement is described in Japanese Patent Application No. HEI 8 (1996)-283281 by the present applicant corresponding to U.S. patent application Ser. No. 08/942,633.

Next, the corneal shape measurement will be described hereinafter. After changing the measurement mode to the corneal shape measurement mode, alignment is to be completed in the aforementioned way, and then the measurement is started by depressing the measurement switch 74. The control circuit 50 turns off the anterior part illumination light source 29 and, at the same time, turns on the light sources 27 for measurement so as to project ring patterns onto the cornea. The control circuit 50 also activates the driving device 37b in order to adjust the diaphragm to the predetermined radius. Thereby the focal depth of the image taken by the CCD camera 38 becomes deeper, accordingly the image having ring patterns projected onto the eye E is clearly photographed as a sharp image all over the cornea of the eye E.

The images of the ring patterns and the alignment target image photographed by the CCD camera 38 are stored into the frame memory 71. The images stored into the frame memory 71 is to be given the edge detecting processing by an image processing circuit 72, and then the processed data is stored into a memory 73 through the control circuit 50.

Figure 6:
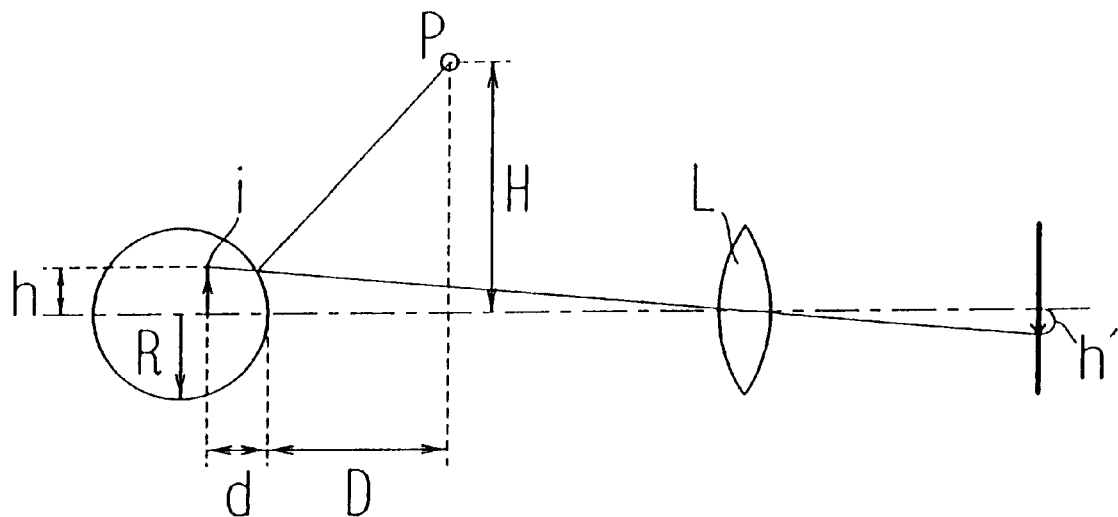
FIG. 6 is a view for illustrating a method for calculating the corneal curvature.

The control circuit 50 calculates the corneal curvature at intervals of the predetermined angle on the basis of the the edge positions of the stored data. The calculation for the corneal curvature can be carried out as follows. As shown in FIG. 6, the detected height is defined as "h'" at the time when image i due to the corneal convex surface of the light source P at the distance D on the optical axis and the height H from the cornea is formed on the two-dimensional detecting plane by the lens L, and the magnification of the optical system of the apparatus is defined as "m", then the corneal curvature radius R is given by following expression;

$$R=(2D/H)mh'.$$

(For the details of this calculation, see U.S. Pat. No. 5,500, 697 corresponding to the Japanese Patent Application No. HEI 7(1995)-124113.)

It is also possible to adapt the following simplified calculation method. The curvature radius of the area where the j-th ring is projected onto the cornea is defined as $Rj$, the proportional constant which is determined by the height of the j-th ring, the distance up to the eye E and the photographing magnification is defined as $Kj$, and the image height on the photographing plane is defined as $hj$, the relationship expression as described above is given by following expression;

$$Rj=kj \cdot hj.$$

Where, if plural model eyes having different curvatures which cover the measurement range is measured in advance, then the proportional constant $Kj$ is obtained as a characteristic value of the apparatus, therefore if it is read and utilized for calculation upon measurement, then the distribution of the curvature is obtained in extremely short time.

In the case the continuous measurement mode for measuring both a cornea shape and a refractive power is selected, by depressing the measurement switch 74 after the completion of the alignment with utilizing the blur of the target image 65, the refractive power measurement is executed first, and then the diaphragm 37a is adjusted to the predetermined radius so that the corneal shape measurement is to be started following the refractive power measurement (the order of executing the measurements can be reversed. However, in the case of the apparatus having a structure in which a visible light (red light) is utilized to project ring patterns, the refractive power measurement should be performed prior to the other measurement in order to avoid miosis).

According to the aforementioned embodiment, the examiner is to depress the measurement (starting) switch 74 to start the measurement, however, an arrangement can be made so as to start the measurement automatically when the apparatus judges that the alignment condition is under the predetermined completion condition on the basis of the positions of the target image 65 and its blurred quantity (from the blurred quantity, the direction of the working distance can be obtained). Further, by adding a driving system for shifting the optical system in X (horizontal) direction, Y (vertical) direction and Z (back and forth) direction, it is made to be possible to carry out alignment by driving the optical system in X, Y and Z directions as well as automatic following on the basis of the detected information of the target image 65.

When the alignment in the direction of the working distance is to be made precisely, such can be applied that projects alignment targets of an infinite distance and of a finite distance are projected onto the cornea of the eye E, and detects the height of the respective alignment target images in order to make them have a predetermined relationship with each other (see U.S. Pat. No. 5,463,430 corresponding to Japanese Patent Application No. HEI 6(1994)-46999). On the other hand, when the accuracy in alignment in the direction of the working distance is not strongly required, an alinement can be easily made by utilizing the blur of the target image as the standard for the judgement. For example, in the eye refractive power measurement, comparatively rough alignment is acceptable, therefore, the alignment method utilizing the blur of the target image can be applied.

In addition, although in the preferred embodiment, the diaphragm 37*a* is to have an aperture of which radius is variable, it is possible to insert and/or retract diaphragms having predetermined radius, which is required for a measurement to and/or from the optical path.

Further, it is described that the diaphragm 37*a* is to be positioned at the back focal point so as to form a telecentric optical system. However, if it is satisfactory only to make the focal depth comparatively deeper, the diaphragm 37*a* can be positioned close to the photographing lens 36 instead.

Figure 7:
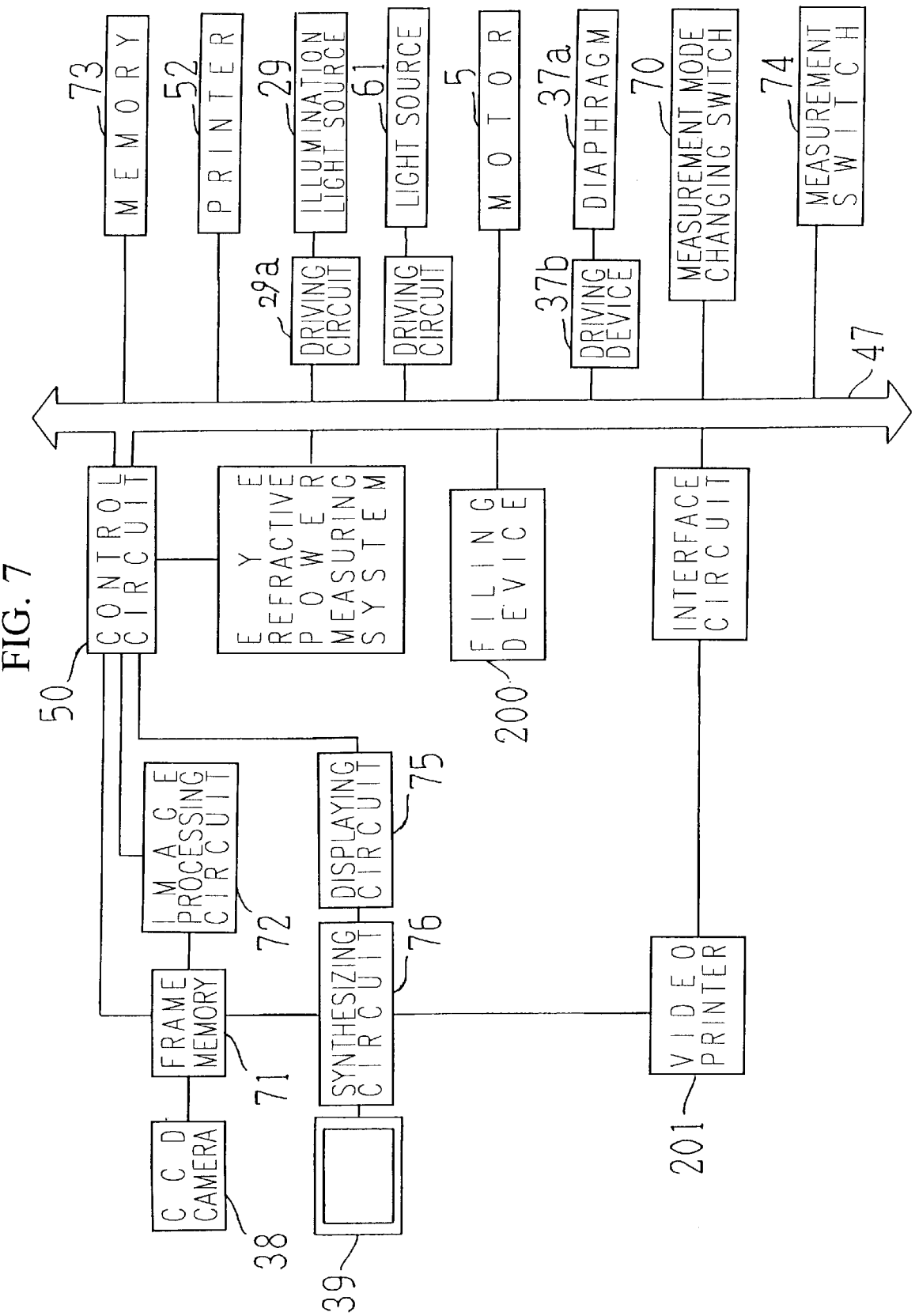
FIG. 7 is a view showing a schematic block diagram of a signal processing system of an apparatus according to the second preferred embodiment of this invention.

FIG. 7 is a view showing a schematic block diagram of a signal processing system of an apparatus according to the second preferred embodiment. The same components as in the first preferred embodiment are indicated by the same numbers. The optical system of the second embodiment basically has the same structure as that of the first preferred embodiment, therefore, the explanation regarding the optical system will not be repeated here.

In the case that the eye refractive power measurement mode is selected, simultaneously it is changed to the photographing mode. As described in the first preferred embodiment, after alignment is completed with observing the alignment image, the measurement (starting) switch 74 is to be depressed. Responding to the signal inputted from the measurement (starting) switch 74, the apparatus carries out the refractive power measurement in the aforementioned way, and the control circuit 50 controls the driving circuit 29*a* in order to increase the quantity of the illumination light emitted from the illumination light source 29 at the anterior part of the eye E, at the same time, the diaphragm 37*a* is adjusted to the predetermined radius for photographing. Since the diaphragm 37*a* is at a position forming a telecentric optical system in object space, the size of the anterior part is to be sharply photographed by the CCD camera 38 due to the little influence from the difference in photographing positions owing to the deep focal depth. The image photographed by the CCD camera 38 is stored into the frame memory 71 in the form of static image after the A/D conversion.

Figure 8:
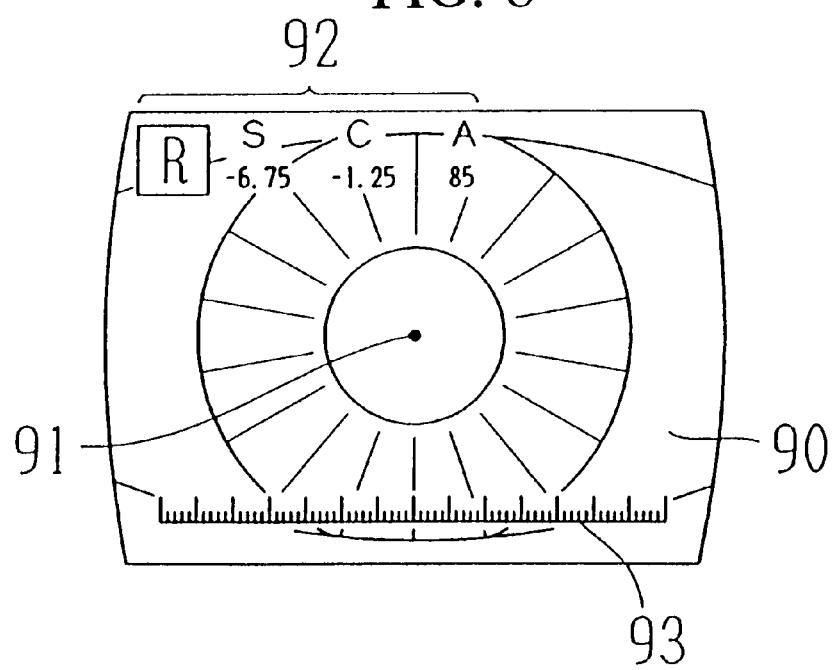
FIG. 8 is a view showing a display example of an image of anterior part of an eye photographed by the apparatus according to the second preferred embodiment of this invention.

The image stored in the frame memory 71 is to be given the D/A conversion, then is displayed on the TV monitor 39 via the image synthesizing circuit 76. FIG. 8 is a view showing a display example of an image at the time. An image of the anterior part 90 and an alignment target image 91 are displayed on the screen as well as the result of the refractive power measurement 92 and the scale 93 to be used as a standard scale for the size of the photographed image. The result of the refractive power measurement 92 and the scale 93 are generated in the display circuit 75 and synthesized with the photographed image in the image synthesizing circuit 76. The divisions of the scale 93, which is generated in the display circuit 75, is marked based on the photographing magnification of the photographing optical system of the apparatus.

The examiner is able to perform measurements for the pupil diameter, the cornea diameter and the like upon the refractive power measurement utilizing the scale 93 and the static image of he anterior part 90 displayed on the screen. Since the target image 91 showing the center of the cornea is also displayed along with the image of the anterior part 90, the examiner is able to grasp the relationships between the center of the cornea and the form of the pupil or the iris, which is helpful information upon diagnosis.

Further, it is also possible that the image of the anterior part stored into the frame memory can be converted into numerical data and displayed by making the image processing circuit 72 and the control circuit 50 calculate, in a well-known method, the cornea diameter, the pupil diameter, the positional information of the center of the cornea and the pupil, and the like.

The scale 93 can be formed optically and be photographed together with the image of the anterior part. In this case, only the following are necessary for signal processing, they are the picture signals of the image of the anterior part from the CCD camera 38, the displaying circuit 75 for generating characters and symbols and the image synthesizing circuit 76 for synthesizing the picture signals. The picture signals synthesized by the image synthesizing circuit 76 can be outputted graphically from a video printer 201 for record.

In addition, the image displayed on the TV monitor 39 can be recorded and kept a filing device 200. In this case, the image is to be recorded and kept together with the result 92 and the scale 93, therefore, measurements for the pupil diameter and the like and editing the photographed image can be carried out freely by calling the stored data from the filing device 200. Further, the image stored in the filing device 200 can be printed out from the video printer 201. The printed image includes the scale so that measurements for the pupil diameter and the like are to be performed easily.

It the aforementioned description, the image of the anterior part is to be taken at the time measuring the refractive power as one example, however, it may be taken separately after the alignment based on the alignment target is completed.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic measurement apparatus for observing or measuring an eye to be examined by positioning the apparatus so as to have a predetermined positional relationship with the eye, the ophthalmic measurement apparatus comprising:

alignment target projecting means for projecting an alignment target onto a cornea of the eye;

alignment means provided with a photographing optical system for photographing an image of the projected alignment target by photoelectric imaging elements to perform an alignment based on condition of the alignment target image photographed by said photoelectric imaging elements;

measurement target projecting means for projecting a target for a measurement onto the cornea of the eye;

measurement means for determining a measurement of a corneal shape of the eye based on an image of the projected target for measurement photographed by said photoelectric imaging elements;

focal depth varying means for making a focal depth of the image photographed by said photoelectric imaging elements variable; and changeover means for switching said focal depth, which is made to be variable by said focal depth varying means, upon the alignment and upon the measurement.

2. The ophthalmic measurement apparatus according to claim 1, further comprising:

signal input means for inputting a signal to start the measurement by said measurement means; and controlling means for controlling switching by said changeover means in accordance with the signal inputted by said signal input means.

3. An ophthalmic measurement apparatus for observing or measuring an eye to be examined by positioning the apparatus so as to have a predetermined positional relationship with the eye, the ophthalmic measurement apparatus comprising:

alignment target projecting means for projecting an alignment target onto a cornea of the eye;

alignment means provided with a photographing optical system for photographing an image of the projected alignment target by photoelectric imaging elements to perform an alignment based on condition of the alignment target image photographed by said photoelectric imaging elements;

first measurement means for measuring a first function of the eye by projecting a first target for measurement onto the eye, and also by detecting the first target image;

second measurement means for measuring a second function of the eye by projecting a second target for measurement onto the eye, and also by detecting the second target image utilizing said photoelectric imaging elements;

focal depth varying means for making a focal depth of the image photographed by said photoelectric imaging elements variable; and changeover means for switching said focal depth which is made to be variable by said focal depth varying means, upon the alignment for said second measurement means and the measurement by said second measurement means.

4. The ophthalmic measurement apparatus according to claim 3, wherein said first measurement means is eye refractive power measurement means for measuring a refractive power of the eye; and said second measurement means is corneal shape measurement means for measuring a corneal curvature of the eye.

5. The ophthalmic apparatus according to claim 4, further comprising controlling means for controlling said said changeover means for making the focal depth upon said corneal shape measurement deeper compared with the focal depth upon said eye refractive power measurement.

6. An ophthalmic measurement apparatus for observing or measuring an eye to be examined by positioning the apparatus so as to have a predetermined positional relationship with the eye, the ophthalmic measurement apparatus comprising:

alignment target projecting means for projecting an alignment target onto a cornea of the eye;

alignment means provided with a photographing optical system for photographing an image of the projected alignment target by photoelectric imaging elements to perform an alignment based on condition of the alignment target image photographed by said photoelectric imaging elements;

recording means for recording an image of an anterior part of the eye photographed by said photoelectric imaging elements;

focal depth varying means for making a focal depth of the image photographed by said photoelectric imaging elements variable; and changeover means for switching said focal depth, which is made to be variable by said focal depth varying means, upon the alignment and upon recording by said recording means.

7. The ophthalmic apparatus according to claim 6, wherein said focal depth varying means comprising a diaphragm of which an aperture is variable in a position at which a telecentric system in object space of said photographing optical system is formed.

8. The ophthalmic apparatus according to claim 6, further comprising:

an illumination optical system for illuminating the anterior part of the eye; and illumination light quantity adjustment means for adjusting illumination light quantity emitted by said illumination optical system being synchronized with switching of the focal depth by said changeover means.

9. The ophthalmic apparatus according to claim 6, further comprising scale forming means for forming a scale indicating standard distance with the image to be photographed based on a photographing magnification of said photographing optical system overlapping with the image of the anterior part of the eye recorded by said recording means.

10. The ophthalmic apparatus according to claim 6, further comprising;

recording magnification selecting means for selecting any desired recording magnification of the image of the anterior part to be recorded by said recording means; and image layout setting means for setting an image layout upon recording.

11. The ophthalmic apparatus according to claim 6, further comprising:

memory means for storing the image of the anterior part of the eye photographed by said photoelectric imaging elements;

measuring means for measuring said stored image of the anterior part of the eye; and display means for displaying said stored image of the anterior part of the eye, whereby the image of the anterior part of the eye displayed by said display means being outputted as picture record by said recording means.

* * * * *